(12) United States Patent
Bimbaum

(10) Patent No.: US 6,605,044 B2
(45) Date of Patent: Aug. 12, 2003

(54) CALORIC EXERCISE MONITOR

(75) Inventor: Burton H. Bimbaum, Woodmere, NY (US)

(73) Assignee: Polar Electro Oy, Kempele (FI)

( * ) Notice: Subject to any disclaimer, the term of this patent is extended or adjusted under 35 U.S.C. 154(b) by 48 days.

(21) Appl. No.: 09/894,509

(22) Filed: Jun. 28, 2001

(65) Prior Publication Data

US 2003/0028116 A1 Feb. 6, 2003

(51) Int. Cl.[7] ................................................ A61B 5/02
(52) U.S. Cl. .......................................... 600/500; 482/8
(58) Field of Search ................................ 600/500, 503, 600/481, 513; 482/8, 901

(56) References Cited

U.S. PATENT DOCUMENTS

| | | | |
|---|---|---|---|
| 4,367,752 A | | 1/1983 | Jimenez et al. |
| 4,566,461 A | | 1/1986 | Lubell et al. |
| 4,855,942 A | | 8/1989 | Bianco |
| 5,527,239 A | * | 6/1996 | Abbondanza ............... 482/8 |
| 5,690,119 A | | 11/1997 | Rytky et al. |
| 5,769,755 A | * | 6/1998 | Henry et al. ............... 482/8 |
| 5,891,042 A | | 4/1999 | Sham et al. |
| 5,976,083 A | | 11/1999 | Richardson et al. |
| 6,013,009 A | | 1/2000 | Karkanen |
| 6,026,335 A | | 2/2000 | Atlas |
| 6,135,951 A | | 10/2000 | Richardson et al. |
| 6,229,454 B1 | | 5/2001 | Heikkilä et al. |
| 6,450,922 B1 | * | 9/2002 | Henderson et al. ............... 482/8 |

FOREIGN PATENT DOCUMENTS

JP            100118052        5/1998

\* cited by examiner

Primary Examiner—Mahmoud Gimie
(74) Attorney, Agent, or Firm—Hoffmann & Baron, LLP

(57) ABSTRACT

A caloric exercise monitor and method for monitoring a person's caloric expenditure during exercising. The caloric exercise monitor generally includes a means for measuring the person's heart rate during exercise, an input device for enabling the person to enter an exercise goal, a calculating unit including a mathematical algorithm for calculating a caloric expenditure rate of the person during exercise based on the measured heart rate and a display for displaying an exercise parameter necessary to reach the entered exercise goal based on the calculated caloric expenditure rate. The displayed exercise parameter can be either or both the calories remaining to be expended to reach the entered goal or the remaining exercise time required to reach the entered goal.

35 Claims, 5 Drawing Sheets

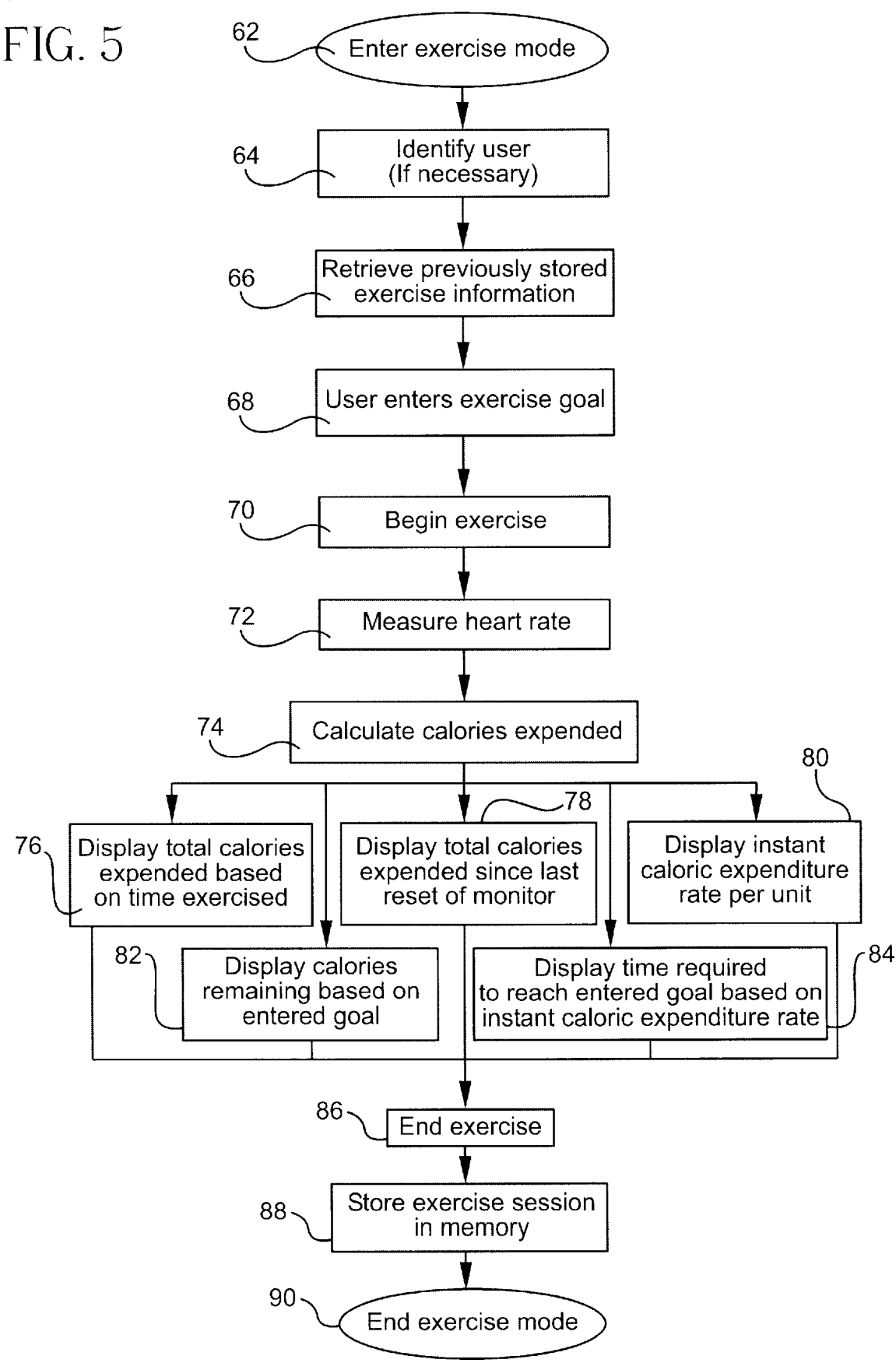

CALORIC EXERCISE MONITOR

FIELD OF THE INVENTION

The present invention relates generally to a caloric exercise monitor and more particularly to a caloric exercise monitor that measures caloric expenditure per unit time based on a user's heart rate and which allows the user to input and monitor an exercise goal during exercise.

BACKGROUND OF THE INVENTION

Currently there are known ambulatory heart rate monitors (HRMs) available, such as Model Nos. M21, M51, S210 and S410 manufactured by Polar Electro Oy of Finland, among others, that calculate calories expended during exercise based on inputted personal information and actual measurement of the user's heart rate. The inputted personal information may include user age, weight, height, sex, self reported activity level, etc. A mathematical formula is then used to calculate calories expended taking into account these factors and the actually measured heart rate of the user during exercise. These HRM's often further supply information to guide an individual, through a variety of indicators and displays, to exercise properly, for example, to exercise within a target heart rate zone or below a maximum heart rate.

The person's heart rate during exercise is measured with the HRM in terms of a heart beat frequency in a given time unit, e.g. beats per minute. The HRM typically includes a chest unit that detects an electrical signal transmitted by the heart and displays the measured heart rate on a display unit. As mentioned above, the display unit can additionally display other indicators, such as calories consumed during exercise and target exercise heart rate zones.

However, none of the prior art HRM devices permit a user to enter an exercise goal and exercise to that goal in an effort to lose weight. Since weight loss is typically a function of inputted calories (caloric content of food ingested) and expended calories (calories burned), knowing differential caloric expenditure during exercise can be of assistance, for example, in designing and maintaining a weight loss program.

Accordingly, it would be desirable to provide an exercise monitor that measures the consumption of calories and that further enables an individual to set an exercise goal and observe how many calories/unit time are being burned and how much more exercise time is required at the current caloric burn rate to complete the exercise goal. It would also be desirable if this monitor could also recall the total calories burned since the last date the monitor's memory was reset.

SUMMARY OF THE INVENTION

The present invention is a caloric exercise monitor for measuring a person's caloric expenditure during exercising. The caloric exercise monitor generally includes means for measuring the person's heart rate during exercise, an input device programmed to enable entry of an exercise goal, such as a caloric expenditure goal or a weight loss goal, and, preferably, pertinent physiological information. The caloric exercise monitor also includes a calculating unit including a mathematical algorithm for calculating a caloric expenditure rate of the person during exercise based on the measured heart rate and a display for displaying an exercise parameter necessary to reach the entered exercise goal based on the calculated caloric expenditure rate.

The exercise parameter displayed to the user can be either or both the number of calories remaining to be expended to reach the entered exercise goal or the remaining exercise time required to reach the entered goal. The display preferably further displays heart rate information and the calculated caloric expenditure rate.

Preferably, the input device is programmed to enable the person to manually enter the exercise goal as well as at least one physiological parameter of the person. Alternatively, the exercise goal and/or the at least one physiological parameter can be wirelessly transmitted or can be uploaded through a computer to the input device. The mathematical algorithm then calculates the caloric expenditure rate based on the measured heart rate and the at least one entered physiological parameter.

In a preferred embodiment, the calculating unit further comprises a timer for measuring the time exercised and the mathematical algorithm calculates the total calories expended during exercise based on the calculated caloric expenditure rate and the measured time exercised. In this case, the display further displays the total calories expended during exercise.

A memory for storing exercise information, calories expended, date and time is also preferably included.

In a method for monitoring an exercise goal during exercise, according to the present invention, an exercise goal, such as a caloric expenditure goal or a weight loss goal, is entered into a caloric exercise monitor. The monitor measures the person's heart rate during exercise and calculates the caloric expenditure rate of the person during exercise based on the measured heart rate. Using the calculated caloric expenditure rate, the monitor displays an exercise parameter indicating what is necessary by the person to reach the entered exercise goal.

The exercise parameter displayed to the user can be either or both the number of calories remaining to be expended to reach the entered exercise goal or the remaining exercise time required to reach the entered goal. The method preferably further includes the steps of displaying heart rate information and displaying the calculated caloric expenditure rate.

Preferably, the method further includes the step of entering at least one physiological parameter of the person into the caloric exercise monitor. The caloric expenditure rate of the person is then calculated based on the measured heart rate and the at least one entered physiological parameter.

In a preferred method, the time exercised is also measured and the total calories expended based on the calculated caloric expenditure rate and the measured time is also calculated. In this case, the method further includes the step of displaying the total calories expended.

In each embodiment, the measured, calculated and/or displayed information can preferably be stored in memory of the monitor.

A preferred embodiment of a caloric exercise monitor and its method of use, as well as other features and advantages of this invention, will be apparent from the following detailed description, which is to be read in conjunction with the accompanying drawings.

BRIEF DESCRIPTION OF THE DRAWINGS

FIG. 5 is a typical flow chart showing the steps performed during the exercise mode of the caloric exercise monitor.

DETAILED DESCRIPTION OF THE PREFERRED EMBODIMENT

The caloric exercise monitor formed in accordance with the present invention is a completely ambulatory device that enables an individual to exercise to his/her exercise goal indoors or outdoors, at home or at a health club, etc. The caloric exercise monitor of the present invention generally includes a heart rate monitor that measures heart rate, for instance, by detecting the heart's ECG signal on the user's chest and displays the measured heart rate on a display typically worn on a wrist unit. Such heart rate monitors have been disclosed in U.S. application Ser. Nos. 09/789,868 and 09/798,577, the specifications thereof being incorporated herein by reference, and include chest units that are wired to a display, chest units that wirelessly transmit heart rate or signals from which heart rate data can be obtained to a display such as a wrist unit, or heart rate monitors that operate solely on the wrist without a chest transmitter.

Figure 1:
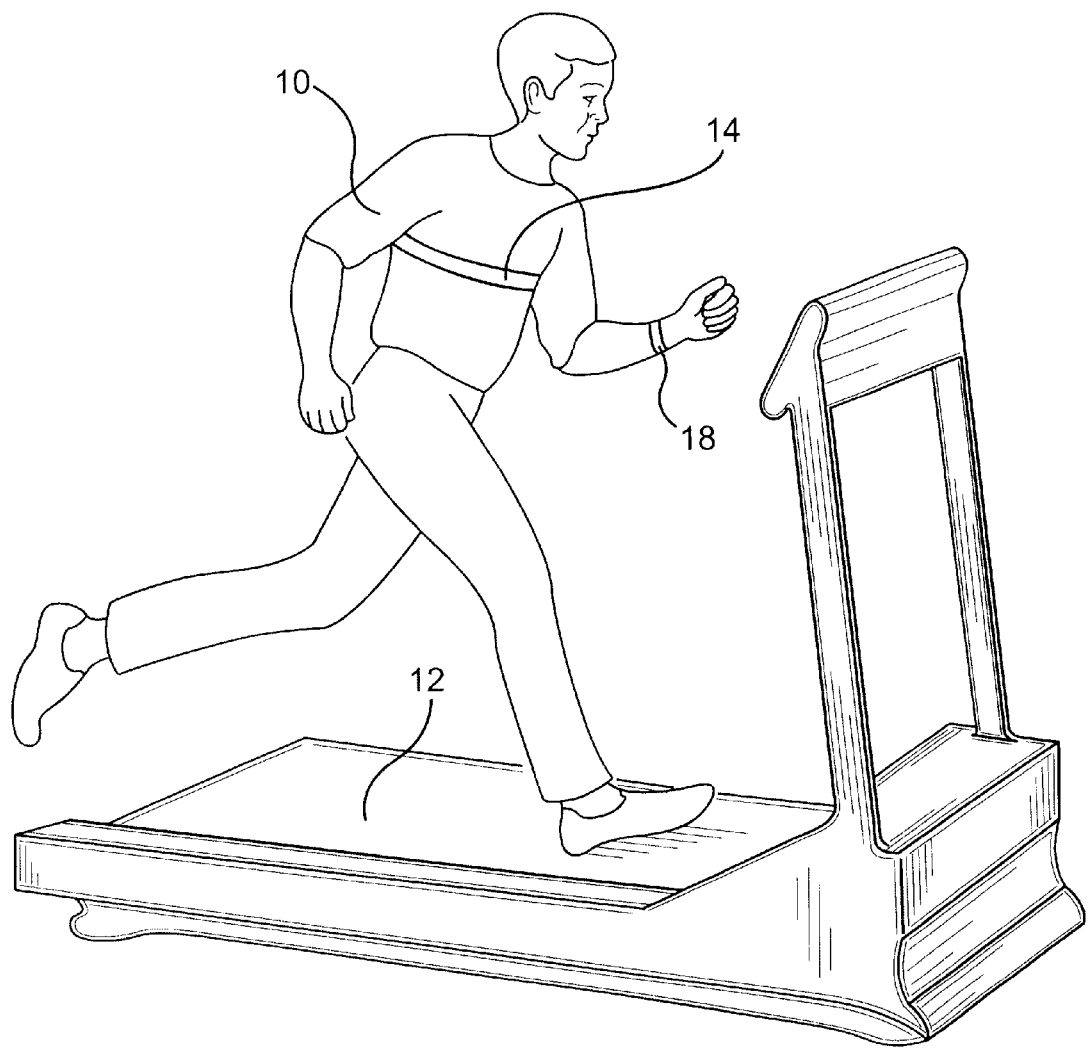
FIG. 1 shows a person using the caloric exercise monitor formed in accordance with the present invention.

FIG. 1 shows a person 10 performing an exercise on a treadmill 12. The heart beat or rate of the person 10 is measured by a transmitter electrode belt 14 to be arranged on the chest. The heart electrical signal is measured by two or more electrodes 16A and 16B provided in the transmitter electrode belt 14, a potential difference being formed there between as the heart beats. The transmitter electrode belt 14 is attached around the person's body e.g. by an elastic band made of an elastic material. The measured heart signal is transmitted preferably inductively to a receiver 18 on the wrist which preferably also comprises a display for displaying the measured heart rate. As mentioned above, the heart rate monitor may also be a mere wrist device wherein the transmitter part and the receiver part are integrated into one device, in which case no transceiver nor receiver electronics is needed. The heart beat may be measured from the wrist by an ECG signal from the arterial pressure pulse or by observing optically the changes in blood flow absorption or reflection, etc.

Figure 2:
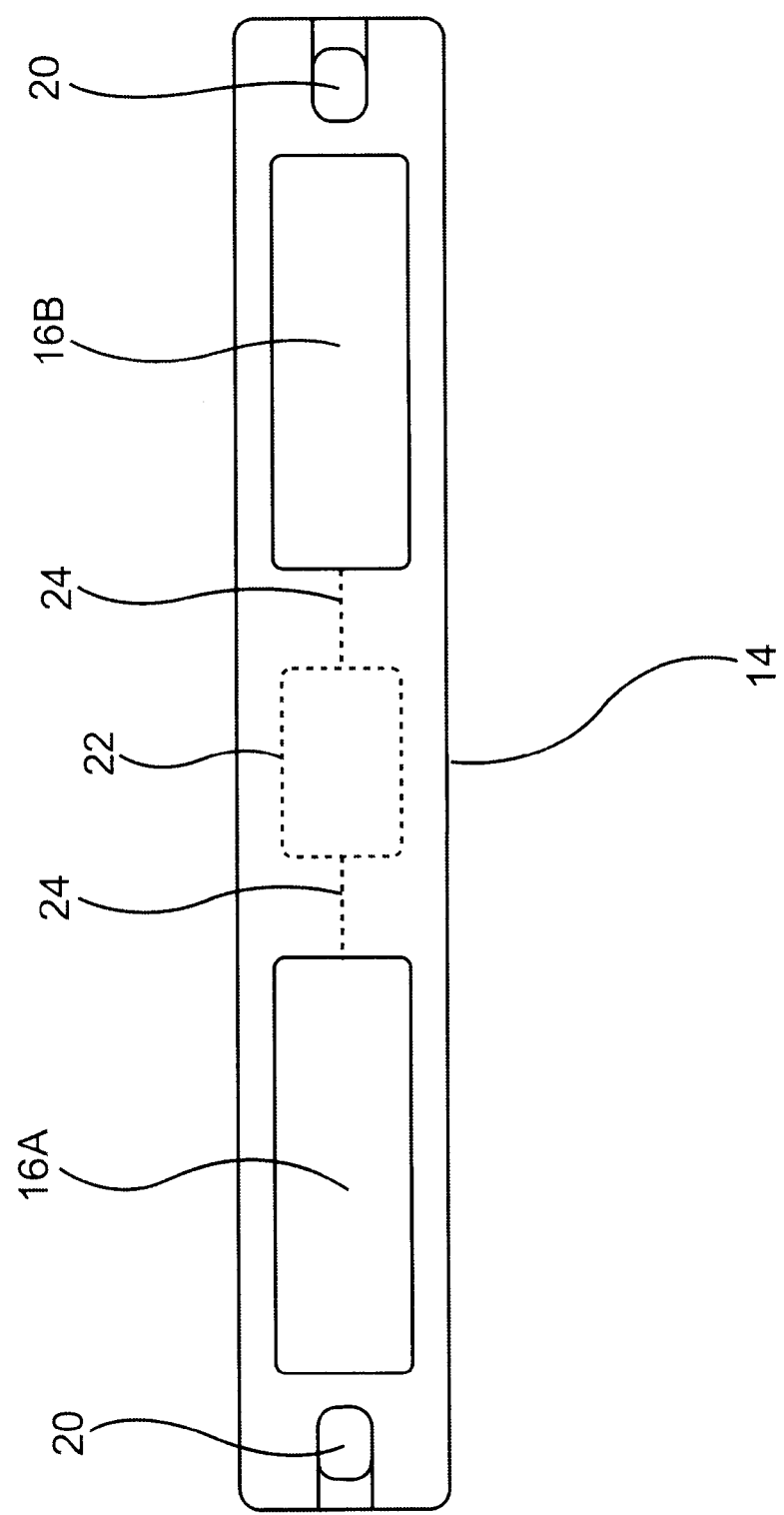
FIG. 2 is a view from the side that touches the body of the electrode belt of the caloric exercise monitor shown in FIG. 1.

FIG. 2 shows in closer detail the electrode belt 14 shown in FIG. 1. In FIG. 2, the electrode belt 14 is shown as seen from the side of the electrodes 16A and 16B, i.e. from the side facing the body. FIG. 2 further shows fasteners 20 by which the electrode belt 14 can be attached to the elastic band, which in turn is strapped around the body. A dotted line in FIG. 2 further designates an electronics unit 22 for processing the heart signal information received from the electrodes 16A and 16B. The electrodes 16A and 16B are electrically connected to the electronics unit 22 by connectors 24.

Figure 3:
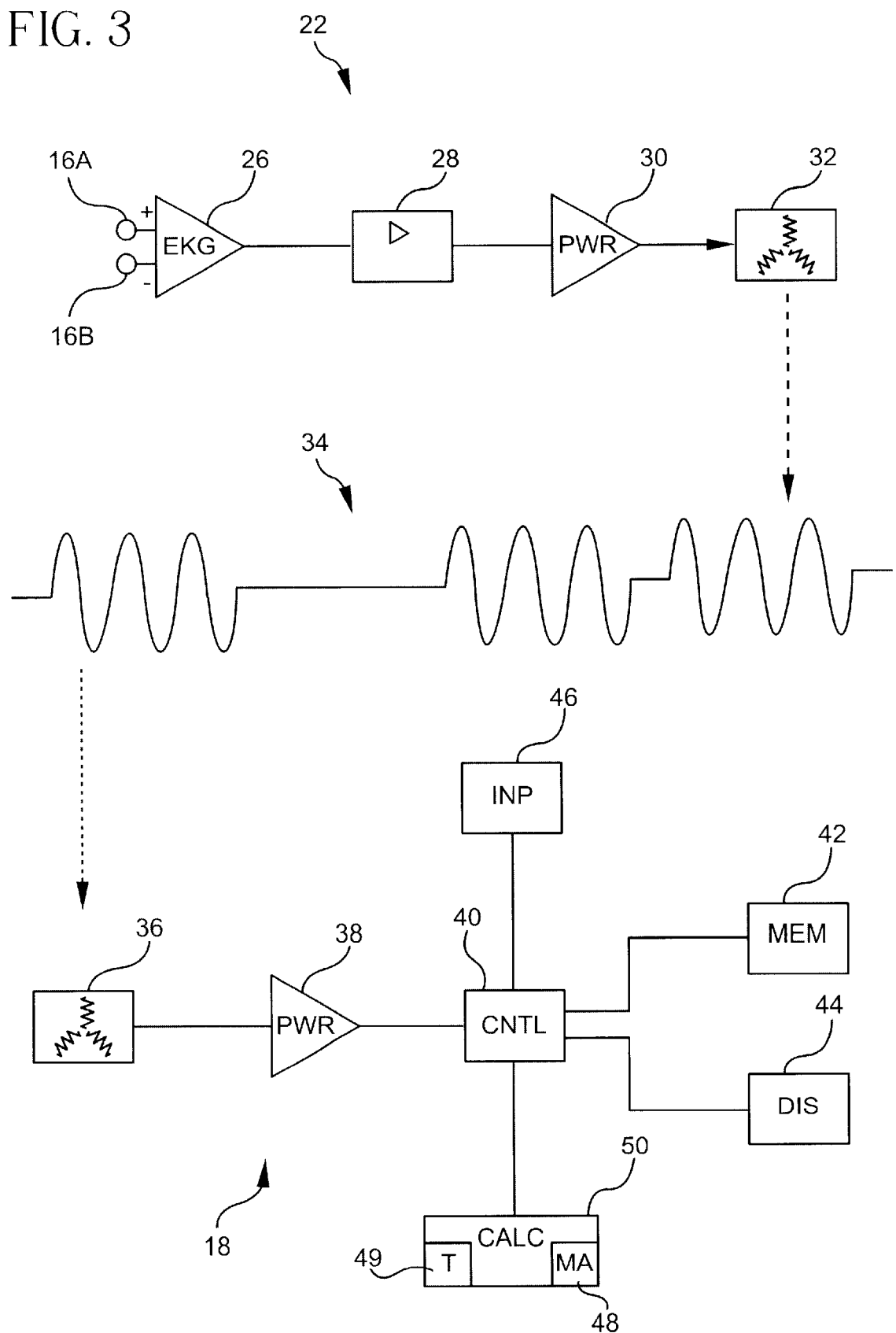
FIG. 3 is a block diagram of the components of the caloric exercise monitor in accordance with the present invention.

FIG. 3 schematically shows the structures of the electronics unit 22 of the transmitter electrode belt 14 and the receiver 18. The electronics unit 22 is shown at the top of the figure, a sample of heart signal or rate information to be transmitted is shown in the middle of the figure, and relevant parts of the receiver unit 18 are shown at the bottom of the figure. The electronics unit 22 of the transmitter electrode belt 14 receives the heart signal information from the electrodes 16A and 16B. From the electrodes, the heart signal is supplied to an ECG-preamplifier 26 wherefrom the signal is transmitted to an amplifier 28 and, through a power amplifier 30, to a transmitter 32. The transmitter 32 is preferably implemented as a coil which inductively transmits heart rate information 34 to the receiver, such as the receiver unit 18 to be arranged on the wrist or e.g. to an external computer.

The heart signal or rate information 34 may be transmitted inductively or, alternatively, may be transmitted optically or through a conductor. In one embodiment, the receiver 18, such as the receiver to be worn on the wrist, comprises a receiver coil 36 wherefrom the received signal is supplied to a central processor 40 via a signal receiver 38. The central processor 40 coordinates the operation of the different parts of the receiver 18. The receiver 18 preferably also comprises a memory 42 for storing heart rate information and an output device, such as a display 49, for indicating or displaying the heart rate and other variables.

The receiver 18 includes an input device 46, such as a keypad, an electronic notepad, pushbuttons, a speech control means, a wireless receiver or a computer link. The input device 46 is used to turn the monitor on and to activate different functional modes of the monitor. The input device 46 of the present invention further enables electronic entry of an exercise goal. The exercise goal can be any exercise target that is convertible to calories, such as a caloric expenditure goal, i.e., the desired number of calories to be expended, a weight loss goal, i.e., the desired number of pounds to be lost, an American College of Sport Medicine (ACSM) fitness category, etc.

The input device 46 further preferably allows the person to electronically enter one or more physiological exercise parameters unique to that person. These physiological parameters may include, but are not limited to, weight, height, age, sex, and self-reported exercise frequency and maximum heart rate.

The exercise goal and physiological parameters can be entered manually by the user, for example, by a keypad, or one or more of these can be monitored and entered wirelessly or via a computer or Internet upload. Such wireless and telemetric data transmission techniques have been described in U.S. Pat. Nos. 5,690,119 and 6,229,454 and U.S. application Ser. No. 09/716,630, the specifications thereof being incorporated herein by reference. Accordingly, the physiological parameters and the user's progress in reaching his or her goal may be remotely monitored, e.g., over the Internet, by someone other than the user, such as a trainer, coach or healthcare professional and the physiological parameters, exercise parameters and goals can be remotely modified, when needed by the other party.

The receiver 18 further includes a calculating unit 50 having a mathematical algorithm 48 and a timer 49 implemented therein and may include a watch with date. The calculating unit 50 does not have to be implemented as a separate device unit. Instead, the calculating unit 50 and the mathematical algorithm 48 and timer 49 therein may be incorporated in the central processor 40. In the preferred embodiment, the mathematical algorithm 48 is implemented by software using a general-purpose processor. However the algorithm may also be implemented as an ASIC, by separate logic components or by employing another such known method.

The mathematical algorithm 48 converts the entered exercise goal to a caloric goal based on known mathematical formulas. For example, if the exercise goal entered is a weight loss goal of 500 grams/week, the mathematical algorithm will convert this goal to a caloric expenditure goal of 3500 kcal/week based on known general standards that to lose 1 kg approximately 7000 kcal must be expended. Where the entered exercise goal is a caloric expenditure goal, no conversion is necessary.

The mathematical algorithm 48 also performs caloric expenditure calculations based on the measured heart rate information 34 received in the receiver 18 and the physiological parameters input by the user 10 through the input means 46 prior to exercising. The mathematical algorithm 48, in conjunction with the timer 49 further continually compares the calculated caloric expenditure to the entered exercise goal so that the person 10 can exercise to that goal. In a preferred embodiment, the mathematical algorithm 48 is a neural network, which is particularly well suited to complex biological modeling situations. The functional operation of the mathematical algorithm 48 and the timer 49 will be discussed in further detail below.

Figure 4:
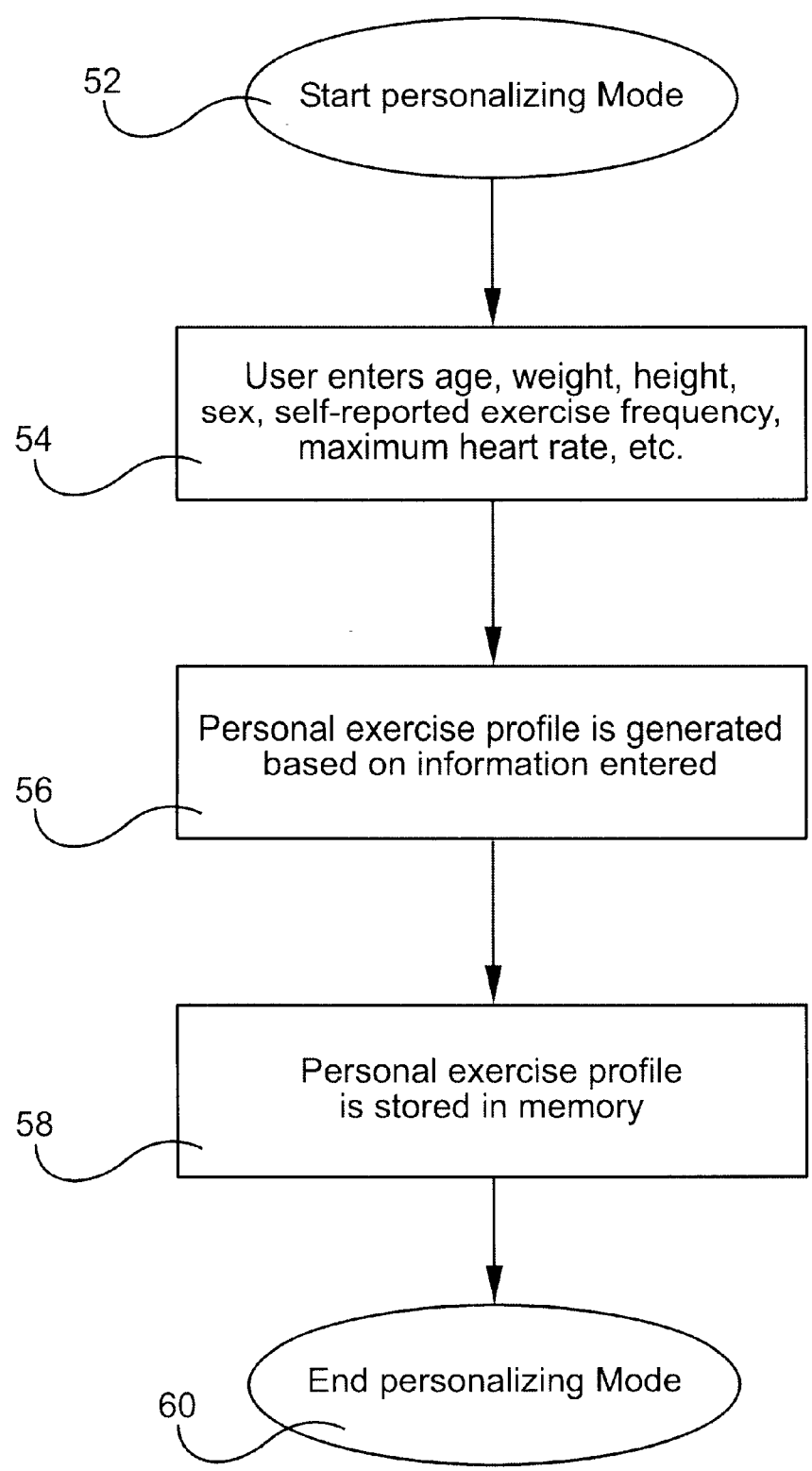
FIG. 4 is a flow chart showing the steps performed during the personalizing mode of the caloric exercise monitor.

FIG. 4 is a flow chart showing the steps of a personalizing phase of the caloric exercise monitor formed in accordance with the present invention. Prior to exercising, the user 10 first starts the personalizing phase in step 52 by selecting a mode/function key of the input device 46. The purpose of the personalizing phase is to set the caloric exercise monitor to the user's unique physiological parameters. Once in the personalizing phase, the user manually enters his/her individual physiological exercise parameters through buttons or keys of the input means 46 in step 54. Alternatively, this information can be inputted via uploading through a computer. The user can view this information on the display 44 as it is entered. Once this information has been entered and verified, a personal exercise profile is generated in step 56 and this profile is then stored in the monitor's memory 42 in step 58. Once the personal exercise profile has been stored, the user ends the personalizing phase by again selecting the appropriate mode/function key of the input means.

FIG. 5 is a flow chart showing the steps followed during an exercise mode of the caloric exercise monitor formed in accordance with the present invention. The exercise mode is entered in step 62 by selecting the mode/function key of the input device 46. If the unit is designed for a sole user, the monitor will automatically retrieve the stored physiological profile information from memory in step 64. If the unit is designed for multiple users, the user is then prompted by the display 44 in step 64 to select a user number identifying the respective physiological profile to be retrieved from memory 42. At this point, the user can also retrieve information relating to previously stored exercise sessions in step 66. This information can be that which has been saved from a specific single exercise session or can be a cumulative log maintained by the user. For instance, where the user is following an overall exercise program wherein an expended calorie goal is desired over a given time frame, as will be discussed in further detail below, the user can store and accumulate the calories expended during each successive exercise session. This cumulative log can then be retrieved from memory at the beginning of each new exercise session and can show calories burned from a specific date and time.

In step 68, the display 44 then prompts the user to enter an exercise goal. The exercise goal entered can be that which is desired for this particular exercise session or can be that which has been retrieved from memory relating to an overall exercise goal. As discussed above, if the entered exercise goal is not in a caloric format, the mathematical algorithm 48 automatically converts the goal to a caloric expenditure goal. At this point, exercise can begin in step 70.

At the start of exercise, the person 10 first activates the timer 49 through the input device 46. As the user exercises, the monitor measures heart rate, as described above, and displays the measured heart rate on the display 44. Based on the measured heart rate and physiological information, the mathematical algorithm 48 calculates the calories being expended taking into account the user's exercise profile. As described in U.S. application Ser. No. 09/789,868, caloric expenditure can be calculated, for example, by an equation according to Formula (1):

$$\text{Cal.} = a + b*HR, \quad (1)$$

wherein "Cal." represents the calories being expended per unit time and "a" and "b" are constants representing a person's physiological parameters and by which the linear dependency between heart rate "HR" and calories expended is determined. It is conceivable that the mathematical algorithm 48 of the present invention can be programmed with preset constants "a" and "b" representing average human physiological parameters or parameters for a particular physiological class or subset. However, for accurate caloric expenditure calculation, it is preferred to have the user enter his/her own unique physiological parameters through the input device 46 as described above. Thus, a truer number of calories being expended per unit time is displayed on the display 44.

By allowing the user to input an exercise target, such as the number of calories the exerciser wishes to burn, the caloric exercise monitor of the present invention further allows the user to monitor and exercise to that goal. In other words, in addition to standard heart rate monitor displays such as heart rate, hi-low alarms, time in exercise zone, and total calories burned, the caloric exercise monitor of the present invention displays current calories/unit time and additional time required to accomplish the preset exercise goal. This can be the number of calories to be burned during the particular exercise session or, for example, number of calories to be burned over a predetermined amount of time.

Specifically, the mathematical algorithm 48 compares the quantity of calories burned at any given time with the user set or converted caloric goal and displays to the user the user's progress on the display 44. By selecting the mode/function key on the input means 46, the user has the option of viewing his/her progress in terms of: (i) total calories expended during this exercise session based on time exercised as measured by the timer 49 (step 76); (ii) total calories expended since last reset of the monitor (step 78); (iii) instant caloric expenditure rate per unit time (step 80); (iv) calories remaining to reach entered goal (step 82); or (v) time required to reach goal based on instant caloric expenditure rate and time exercised (step 84). The following example illustrates the various options in monitoring caloric expenditure according to the present invention.

EXAMPLE

After entering his personal physiological parameters and a caloric expenditure goal of 500 calories for the present exercise session, a person using the caloric exercise monitor according to the present invention begins walking at a rate of roughly 5 mph. The following table shows the information that will be displayed to the user each minute during the course of his exercise:

| (1) Elapsed Exercise Time (measured in minutes) | (2) Average HR (measured in beats/min) | (3) Caloric Expenditure Rate (cal/min = a + b*HR) | (4) Total Calories Expended (Σ(3)I) | (5) Remaining Calories to Reach Goal(Goal (500)–(4)) | (6) Time Remaining to Reach Goal (minutes = (5)/(3)) |
|---|---|---|---|---|---|
| 1 | 96 | 18 | 18 | 482 | 27 |
| 2 | 96 | 24 | 42 | 458 | 20 |
| 3 | 100 | 24 | 66 | 434 | 18 |
| 4 | 100 | 24 | 90 | 410 | 17 |
| 5 | 103 | 26 | 116 | 384 | 15 |
| 6 | 103 | 26 | 142 | 358 | 14 |
| 7 | 105 | 28 | 170 | 330 | 12 |
| 8 | 103 | 26 | 196 | 304 | 12 |
| 9 | 105 | 27 | 223 | 277 | 10 |
| 10 | 105 | 28 | 251 | 249 | 9 |
| 11 | 108 | 29 | 280 | 220 | 8 |
| 12 | 110 | 31 | 311 | 189 | 6 |
| 13 | 110 | 29 | 340 | 160 | 6 |
| 14 | 110 | 30 | 370 | 130 | 4 |
| 15 | 110 | 30 | 400 | 100 | 3 |
| 16 | 110 | 30 | 430 | 70 | 2 |
| 17 | 111 | 31 | 461 | 39 | 1 |
| 18 | 110 | 29 | 490 | 10 | 0 |
| 19 | 111 | 31 | 521 | −21 | −1 |
| 20 | 112 | 30 | 551 | −51 | −2 |

Thus, for instance, after five (5) minutes of exercise, the monitor will display the person's measured heart rate of 103 beats/min and the person's calculated caloric expenditure rate of 26 calories/minute (a+b*103). The calculating unit of the monitor further calculates the total calories expended to that point by summing the caloric expenditure rates over time to arrive at a total of 116 calories expended. The total number of calories expended thus far is then subtracted from the entered caloric expenditure goal of 500 calories resulting in 384 (500–116) as the number of calories remaining to reach the entered caloric expenditure goal. Finally, by dividing the number of calories remaining to reach the entered caloric expenditure goal (384) by the current caloric expenditure rate (26), the monitor can display the remaining exercise time (15 minutes) required to reach the entered caloric expenditure goal. At ten (10) minutes, the person has expended 251 calories and, therefore, must expend an additional 249 calories to reach his goal. At the calculated caloric expenditure rate of 28 calories/minute, the person must exercise an additional 9 minutes to reach his goal. If the person surpasses his goal, the monitor will display the additional calories burned and the surplus of exercise time.

When the user finishes exercising in step 86, the monitor can automatically store the exercise information or the display can prompt the user to store information relating to the exercise session in memory 42 in step 88. This information can include the total calories expended during the session, which can be stored in the user's cumulative log, or can be any other parameter measured during the session, such as maximum/minimum heart rate, maximum/minimum caloric expenditure rate or time remaining to reach the exercise goal. As mentioned above, this information can later be retrieved by the user during a subsequent exercise session.

The invention thus guides the individual to an exercise goal that is preset on an ambulatory monitor prior to beginning the exercise. The unit then calculates how many calories per unit time the individual is currently burning and estimates a time to finish the exercise session based on the preset goal and the current caloric burn rate and may show total calories expended since the last time the monitor was reset.

Although the illustrative embodiments of the present invention have been described herein with reference to the accompanying drawings, it is to be understood that the invention is not limited to those precise embodiments and that various other changes and modifications may be effected therein by one skilled in the art without departing from the scope or spirit of the invention.

What is claimed is:

1. A caloric exercise monitor for monitoring a person's caloric expenditure during exercising comprising:
   means for measuring the person's heart rate during exercise;
   an input device programmed to enable entry of a calory based exercise goal;
   a calculating unit including a mathematical algorithm for calculating the caloric expenditure rate of the person during exercise based on the measured heart rate and for calculating an exercise parameter representing an amount of additional exercise necessary to reach the entered exercise goal based on the calculated caloric expenditure rate; and
   a display for displaying the calculated exercise parameter necessary to reach the entered exercise goal based on the calculated caloric expenditure rate.

2. The monitor as defined in claim 1, wherein the exercise goal is a caloric expenditure goal.

3. The monitor as defined in claim 1, wherein the exercise goal is a weight loss goal.

4. The monitor as defined in claim 1, wherein the input device is programmed to enable the person to manually enter the exercise goal.

5. The monitor as defined in claim 1, wherein the input device is programmed to enable remote entry of the exercise goal.

6. The monitor as defined in claim 1, wherein the input device is farther programmed to enable the person to manually enter at least one physiological parameter of the person, the mathematical algorithm calculating the caloric expenditure rate during exercise based on the measured heart rate and the at least one entered physiological parameter.

7. The monitor as defined in claim 1, wherein the input device is further programmed to enable remote entry of at least one physiological parameter of the person, the mathematical algorithm calculating the caloric expenditure rate during exercise based on the measured heart rate and the at least one entered physiological parameter.

8. The monitor as defined in claim 1, wherein the display further displays heart rate information.

9. The monitor as defined in claim 1, wherein the display further displays the calculated caloric expenditure rate.

10. The monitor as defined in claim 1, wherein the exercise parameter is the number of calories remaining to be expended to reach the entered exercise goal.

11. The monitor as defined in claim 1, wherein the exercise parameter is the remaining exercise time required to reach the entered exercise goal.

12. The monitor as defined in claim 1, wherein the calculating unit further comprises a timer for measuring the time exercised, the mathematical algorithm further calculating the total calories expended during exercise based on the calculated caloric expenditure rate and the measured time exercised.

13. The monitor as defined in claim 12, wherein the display further displays the number of total calories expended.

14. The monitor as defined in claim 1, further comprising a memory for storing exercise information.

15. The monitor as defined in claim 1, further comprising a memory for storing caloric expenditure information.

16. A monitor as defined in claim 1, wherein the display further prompts the person to enter the exercise goal.

17. A method for monitoring an exercise goal during exercise comprising the steps of:

entering a calory based exercise goal into a caloric exercise monitor;

measuring a person's heart rate during exercise with the caloric exercise monitor;

calculating a caloric expenditure rate of the person during exercise based on the measured heart rate;

calculating an exercise parameter representing an amount of additional exercise necessary to reach the entered exercise goal based on the calculated caloric expenditure rate; and displaying the calculated exercise parameter necessary to reach the entered exercise goal based on the calculated caloric expenditure rate.

18. The method as defined in claim 17, wherein the exercise goal is a caloric expenditure goal.

19. The method as defined in claim 17, wherein the exercise goal is a weight loss goal.

20. The method as defined in claim 17, wherein the exercise goal is manually entered by the person.

21. The method as defined in claim 17, wherein the exercise goal is remotely entered.

22. The method as defined in claim 17, further comprising the step of entering at least one physiological parameter of the person into the caloric exercise monitor and wherein the caloric expenditure rate of the person is calculated based on the measured heart rate and the at least one entered physiological parameter.

23. The method as defined in claim 22, wherein the at least one physiological parameter of the person is manually entered into the caloric exercise monitor by the person.

24. The method as defined in claim 22, wherein the at least one physiological parameter of the person is remotely entered into the caloric exercise monitor.

25. The method as defined in claim 17, further comprising the step of displaying heart rate information.

26. The method as defined in claim 17, further comprising the step of displaying the caloric expenditure rate.

27. The method as defined in claim 17, wherein the exercise parameter is the number of calories remaining to be expended to reach the entered exercise goal.

28. The method as defined in claim 17, wherein the exercise parameter is the remaining exercise time required to reach the entered exercise goal.

29. The method as defined in claim 17, further comprising the step of measuring the time exercised; and calculating the total calories expended based on the calculated caloric expenditure rate and the measured time exercised.

30. The method as defined in claim 29, further comprising the step of displaying the number of total calories expended.

31. The method as defined in claim 17, further comprising the step of storing exercise information in memory.

32. The method as defined in claim 17, further comprising the step of storing total calories expended since last reset.

33. The method as defined in claim 17, further comprising the step of storing the last reset date and time in memory.

34. The method as defined in claim 17, further comprising the step of remotely monitoring the person's caloric expenditure rate and exercise parameter.

35. The method as defined in claim 17, further comprising the step of prompting the person with the caloric exercise monitor to enter the exercise goal therein.

* * * * *

UNITED STATES PATENT AND TRADEMARK OFFICE
CERTIFICATE OF CORRECTION

PATENT NO. : 6,605,044 B2
DATED : August 12, 2003
INVENTOR(S) : Birnbaum

It is certified that error appears in the above-identified patent and that said Letters Patent is hereby corrected as shown below:

Title page,
Item [12], should read

-- [12] United States Patent
     Birnbaum --.

Column 8,
Line 36, "device is farther" should read -- device is further --.

Signed and Sealed this

Sixth Day of January, 2004

JAMES E. ROGAN
*Director of the United States Patent and Trademark Office*

UNITED STATES PATENT AND TRADEMARK OFFICE
CERTIFICATE OF CORRECTION

PATENT NO. : 6,605,044 B2
DATED : August 12, 2003
INVENTOR(S) : Birnbaum

It is certified that error appears in the above-identified patent and that said Letters Patent is hereby corrected as shown below:

Title page,
Item [12], now reads "[12] United States Patent Bimbaum" should read -- [12] United States Patent Birnbaum --.

Item [75], now reads "[75] Inventor: Burton H. Bimbaum" should read
[75] Inventor: Burton H. Birnbaum --.

Column 8,
Line 36, now reads "device is farther" should read -- device is further --.

Signed and Sealed this

Twenty-seventh Day of April, 2004

JON W. DUDAS
*Acting Director of the United States Patent and Trademark Office*